United States Patent
Merenov et al.

(10) Patent No.: US 9,090,540 B2
(45) Date of Patent: Jul. 28, 2015

(54) PROCESS FOR THE PRODUCTION OF METHYLENE DIPHENYL DIISOCYANATE ISOMER MIXTURES WITH SPECIFIC ISOMER DISTRIBUTIONS AND NEW PRODUCTS DERIVED

(75) Inventors: Andrei S. Merenov, Lake Jackson, TX (US); Dennis W. Jewell, Angleton, TX (US); Paul A. Gillis, Lake Jackson, TX (US); Gerard I. Jansma, Krewerd (NL); Ashley W. Breed, Lake Jackson, TX (US); John J. Anderson, Midland, MI (US); Daniel J. Reed, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 122 days.

(21) Appl. No.: 13/814,981

(22) PCT Filed: Sep. 20, 2011

(86) PCT No.: PCT/US2011/052332
§ 371 (c)(1),
(2), (4) Date: Feb. 8, 2013

(87) PCT Pub. No.: WO2012/040187
PCT Pub. Date: Mar. 29, 2012

(65) Prior Publication Data
US 2013/0172604 A1   Jul. 4, 2013

Related U.S. Application Data

(60) Provisional application No. 61/386,283, filed on Sep. 24, 2010.

(51) Int. Cl.
*C07C 263/20* (2006.01)
*C07C 263/10* (2006.01)

(52) U.S. Cl.
CPC ............. *C07C 263/20* (2013.01); *C07C 263/10* (2013.01)

(58) Field of Classification Search
None
See application file for complete search history.

(56) References Cited

U.S. PATENT DOCUMENTS

| 7,038,002 | B2 | 5/2006 | Pirkl et al. | |
| 7,495,124 | B2 * | 2/2009 | Pirkl et al. | 560/352 |
| 7,649,108 | B2 * | 1/2010 | Schal et al. | 560/352 |

FOREIGN PATENT DOCUMENTS

EP   1792895 A1   6/2007

OTHER PUBLICATIONS

PCT/US2011/052332, International Preliminary Report on Patentability dated Mar. 26, 2013.
PCT/US2011/052332, Written Opinion of the International Search Authority dated Mar. 24, 2013.
PCT/US2011/052332, International Search Report dated Mar. 29, 2012.

* cited by examiner

*Primary Examiner* — Karl J Puttlitz

(57) ABSTRACT

The present invention a process and apparatus for the production of methylene diphenyl diisocyanate (MDI) isomer mixtures with a low 2,2'-MDI isomer content and a high 2,4'-MDI isomer content. The resulting mixtures have an increased reactivity and are acceptable in food grade application due to the reduction in primary aromatic amines formed during the curing process. The process and apparatus also include controlling the amount of 4,4'-MDI, which is the most reactive isomer in the mixture allowing use in a wide variety of applications.

12 Claims, 2 Drawing Sheets

US 9,090,540 B2

PROCESS FOR THE PRODUCTION OF METHYLENE DIPHENYL DIISOCYANATE ISOMER MIXTURES WITH SPECIFIC ISOMER DISTRIBUTIONS AND NEW PRODUCTS DERIVED

BACKGROUND OF THE INVENTION

1. Field of the Invention

Embodiments of the present invention generally relate to a process and apparatus for the production of methylene diphenyl diisocyanate (MDI) isomer mixtures with low 2,2'-MDI isomer content and high 2,4'-MDI isomer content.

2. Description of the Related Art

Mixtures of methylene diphenyl diisocyanate (MDI) isomers are widely used in the preparation of polyurethane film composites and adhesives. During the preparation of film composites or adhesives, an MDI mixture reacts with a polyol (e.g., polyether polyol) to form polyurethane. Generally, an excess of MDI is used to ensure the completion of the reaction. However, non-reacted MDI can diffuse to the surface of the film composite or adhesive, where it may be hydrolyzed into a primary aromatic amine. This creates a problem in certain applications, such as product packaging in the food industry because there are strict requirements regulating the amount of primary aromatic amines in food packaging materials.

Conventional MDI processes produce three isomers, i.e., 4,4'-MDI, 2,4'-MDI, and 2,2'-MDI. Other products of conventional MDI processes are heavier molecular weight isocyanates, commonly called polymeric MDI (PMDI). The most reactive MDI isomer is 4,4'-MDI, and the least reactive is 2,2'-MDI. Thus, among MDI isomers, 2,2'-MDI requires the longest time for conversion, and the overall reactivity of an MDI isomer mixture increases as the 2,2'-MDI isomer content is reduced. However, the ratio of 2,2'-MDI and 2,4'-MDI to 4,4'-MDI also controls the viscosity of the prepolymer. That is, prepolymer viscosity decreases as the ratio of 2,2'-MDI and 2,4'-MDI to 4,4'-MDI increases. Thus, mixtures with a high amount of 2,4'-MDI and a low amount of 2,2'-MDI are used in applications requiring low viscosity prepolymers, particularly in the food industry.

Therefore, as the demand for low viscosity prepolymers increases, such as for food applications, there is a need for improved methods and apparatus for producing MDI isomer mixtures with low 2,2'-MDI content and high 2,4'-MDI content.

SUMMARY OF THE INVENTION

In one embodiment, a process for the production of a mixture of methylene diphenyl diisocyanate (MDI) isomers comprises forming methylene diphenyl diamines and polyamines of the diphenylmethane series by reacting aniline and formaldehyde in the presence of an acid catalyst, phosgenating the methylene diphenyl diamines and polyamines of the diphenylmethane series to produce a mixture of the MDI isomers and polymeric MDI, separating from the mixture of the MDI isomers and the polymeric MDI a first fraction containing at least 98% by weight of the MDI isomers comprising at least 52% by weight of 2,4'-MDI and 2,2'-MDI based on the total weight of the first fraction, and separating from the first fraction a second fraction containing at least 99% by weight of the MDI isomers comprising at least 52% by weight of 2,4'-MDI based on the total weight of the second fraction.

In another embodiment, apparatus for separating from a mixture of MDI isomers and polymeric MDI a fraction containing at least 98% by weight MDI isomers comprising at least 52% by weight 2,4'-MDI and 2,2'-MDI based on the total weight of the fraction comprises a distillation column having a separation section and an integrated side rectification section and a reboiler positioned to receive bottoms from the distillation column and send 4,4'-MDI to the integrated side rectification section.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention generally relate to a process and apparatus for the production of methylene diphenyl diisocyanate (MDI) isomer mixtures with low 2,2'-MDI isomer content and high 2,4'-MDI isomer content. The resulting mixtures have an increased reactivity and are acceptable in food grade applications due to the reduction in primary aromatic amines formed during the curing process. The process and apparatus also include controlling the amount of 4,4'-MDI, which is the most reactive isomer in the mixtures allowing use in a wide variety of applications.

Figure 1:
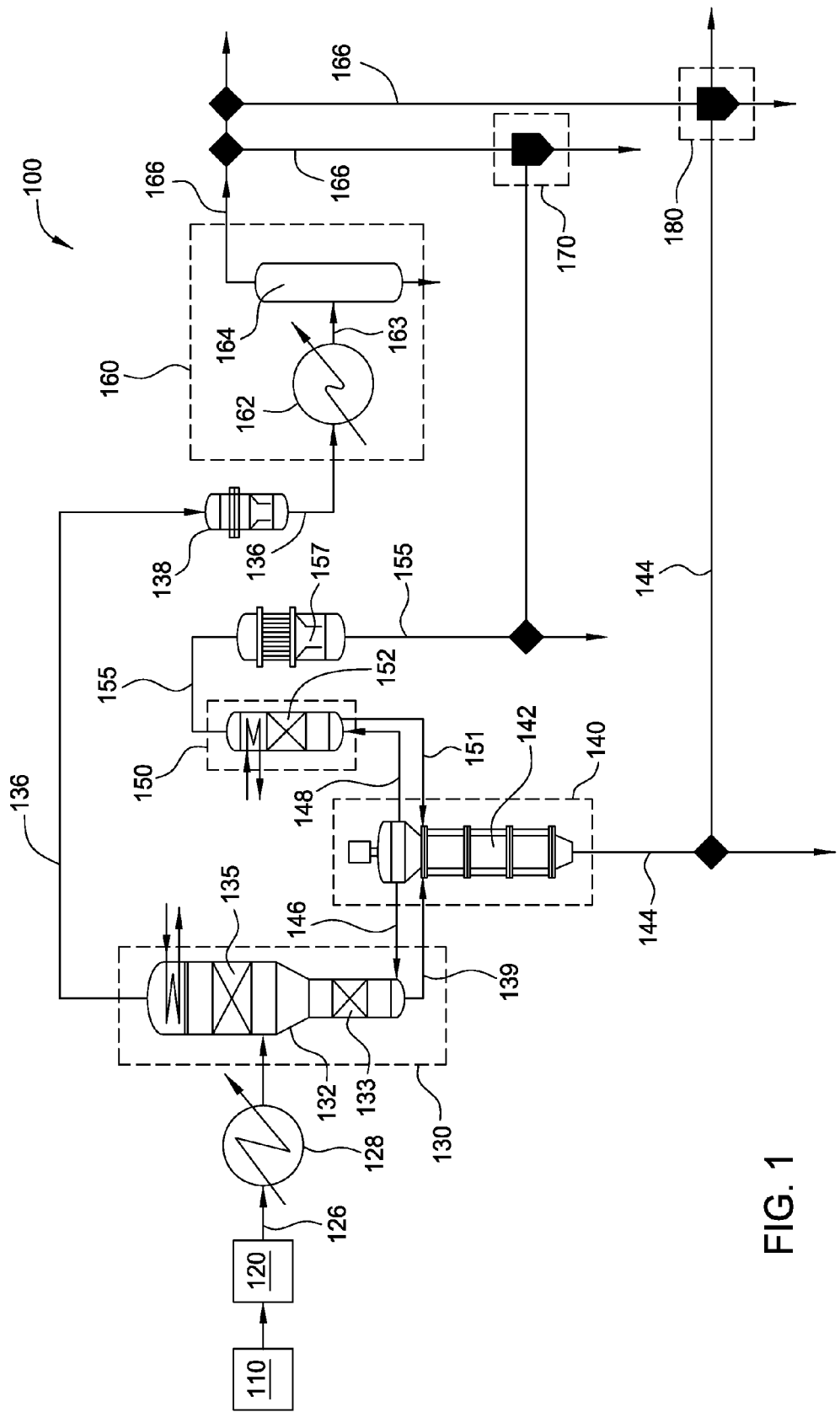
FIG. 1 is a schematic depiction of an apparatus and process 100 according to one embodiment.

FIG. 1 is a schematic depiction of an apparatus and process 100 according to one embodiment. At box 110, a polyamine or polyamine mixture of a diphenylmethane series is formed conventionally by condensing aniline and formaldehyde in the presence of an acid catalyst. Suitable polyamine mixtures of the diphenylmethane series are obtained by condensation of aniline and formaldehyde in a quantitative molar ratio from about between about 20:1 and about 1.6:1 and a quantitative ratio of aniline to acid catalyst from between about 20:1 and about 1:1.

Generally formaldehyde is used as an aqueous solution with water content between about 1% and about 95% by weight, based on the total weight of the solution. Alternatively, other compounds supplying methylene groups (e.g., polyoxymethylene glycol, para-formaldehyde, and trioxane) may be used.

Strong acids, particularly inorganic acids, are suitable as acid catalysts for the reaction of the aniline and formaldehyde. Suitable acids include hydrochloric acid, sulfuric acid, phosphoric acid, and methane sulfonic acid. Solid acid catalysts, such as organic and inorganic ion exchangers, acid silicon/aluminum mixed oxides, and acid zeolites may also be used.

In one embodiment, aniline and the acid catalyst are first mixed together. The mixture of aniline and the acid catalyst are then mixed with formaldehyde at temperatures between about 20° C. and about 100° C., and a preliminary reaction is carried out.

Alternatively, aniline and formaldehyde are first mixed at temperatures between about 5° C. to about 100° C. in the absence of the acid catalyst. In such an example, condensation products of aniline and formaldehyde are formed (i.e., aminal). On completion of the aminal formation, water present in the reaction mixture may be removed by phase separation or by other suitable procedures, such as distillation. The condensation product is then mixed with an acid catalyst, and a preliminary reaction is carried out at a temperature of about 20° C. to about 100° C.

In either case, the temperature of the reaction mixture is then raised, either in stages or continuously, to a temperature of from about 100° C. to about 250° C. The reaction mixture is then neutralized with a base, such as hydroxides of alkali metals and alkaline earth metals (e.g., sodium hydroxide).

After neutralization, the organic phase is separated from the aqueous phase by suitable methods. The product that contains the organic phase remaining after the separation of the aqueous phase is subjected to a wash procedure to form a purified organic phase. The purified organic phase is then freed from excess aniline and other substances present in the mixture by suitable physical separation methods, such as distillation, extraction, or crystallization.

The polyamine of the diphenyl methane series obtained from the process associated with box 110 is then conventionally reacted with phosgene in an inert organic solvent to form corresponding isocyanates in box 120. Suitable inert solvents include chlorinated, aromatic hydrocarbons, such as monochlorobenzene, dichlorobenzenes, trichlorobenzenes, corresponding toluenes and xylenes, as well as chloroethybenzene. The phosgenation is carried out at temperatures from about 50° C. to about 250° C. and at pressures ranging from ambient pressure to about 50 bar.

After phosgenation, the excess phosgene, any inert organic solvent, the HCL formed, and/or mixtures thereof, are separated from the reaction mixture, such as by distillation. As a result, a crude diisocyanate and polyisocyanate (i.e., crude MDI feedstock 126) is obtained in box 120.

Next, the crude MDI feedstock 126, containing both methylene diphenyl diisocyanate (MDI) isomers and polymeric methylene diphenyl diisocyanate (PMDI) is heated to a temperature of between about 170° C. and about 260° C. in a heat exchanger 128. Generally, in box 130, the lower boiling point components (i.e., 2,2'-MDI and 2,4'-MDI) are separated from the higher boiling point components (i.e., 4,4'-MDI and PMDI). In one embodiment of box 130, the preheated feedstock enters a distillation column 132. The distillation column 132 includes both a stripping section 133 and a rectification section 135. In one embodiment, the stripping section 133 is maintained at a temperature between about 100° C. and about 260° C. and a pressure between about 0.6 mmHg and about 50 mmHg. The rectification section 135 may be maintained at a temperature between about 50° C. and about 200° C. and a pressure between about 0.5 mmHg and about 20 mmHg.

The lower boiling point components, i.e., 2,2'-MDI and 2,4'-MDI, are recovered above the stripping section 133 of the distillation column 132 after purification in the rectification section 135 of the distillation column 132. As a result, a 2,4'-MDI rich mixture 136 exits the distillation column 132 and passes through a condenser 138. The 2,4'-MDI rich mixture 136 has a fraction containing at least 98% by weight of MDI isomers with a content of at least 52% by weight of a mixture of 2,4'-MDI and 2,2'-MDI based on the total weight of the fraction. In one embodiment, the 2,4'-MDI rich mixture 136 has a fraction containing at least 98% by weight of MDI isomers with a content of 4,4'-MDI of from 5% to 48% by weight, a content of 2,4'-MDI of from 52% to 95% by weight, and a content of 2,2'-MDI of from 0.01% to 20% by weight.

The mixture of the higher boiling point components (i.e., 4,4'-MDI and PMDI) are removed from the distillation column 132 as bottoms 139 and passed through an evaporative reboiler 142 at box 140. The evaporative boiler 142 is maintained at a temperature between about 100° C. and about 260° C. and a pressure between about 3 mmHg and about 30 mmHg. The bottom product of the evaporative reboiler 142 is PMDI with a reduced amount of MDI isomers and is removed from the evaporative reboiler 142 as a PMDI stream 144. The PMDI stream 144 can be used as a component in rigid and flexible polyurethane foam applications. In the evaporative reboiler 142, a portion of the mixture is evaporated, and a portion of the vapors is returned to the distillation column 132 as a boil-up stream 146.

The remainder of the vapors exits the evaporative reboiler 142 as stream 148, where it enters a side rectifier 152 at box 150. The side rectifier 152 is maintained at a temperature between about 50° C. and about 260° C. and a pressure between about 1 mmHg and about 29 mm Hg. In the side rectifier 152, 4,4'-MDI is separated from traces of PMDI remaining in the vapor. As a result, a purified 4,4'-MDI stream 155 exits the side rectifier 152 and is passed through a quench condenser 157 at a temperature between about 40° C. and about 50° C. The purified 4,4'-MDI stream 155 includes at least 98.5% by weight content of 4,4'-MDI. Bottoms 151 from the side rectifier 152 are recycled into the evaporative reboiler 142.

In box 160, the 2,4'-MDI rich mixture 136 enters a heat exchanger 162, where it is heated to between about 150° C. and about 190° C. The resulting preheated stream 163 enters a separator 164, such as another distillation column. The separator 164 may include a partial vapor-liquid condenser and a kettle-type reboiler. In one embodiment, the reboiler and condenser have a separation power of a single theoretical stage. The separator 164 may have between about 5 and about 20 theoretical stages. In one embodiment, the separator 164 has ten theoretical stages (e.g., five stages above the feed and five stages below the feed). In this embodiment, the preheated stream 163 may enter the separator 164 on the fifth stage. In one example, the separator 164 operates with a molar reflux ratio of between about 2 and 10, such as about 5.98 and a bottom to feed mass ratio of between about 0.5 and about 0.9, such as about 0.73. The operating pressure of the separator 164 may be between about 0.5 mmHg and about 5.0 mmHg, such as about 2.0 mmHg, in the partial condenser and between about 3 mmHg and about 10 mmHg, such as about 5.8, mmHg in the reboiler.

In box 160, at least 50% of the 2,2'-MDI is removed from the entering stream and exits the separator 164 in a 2,2'-MDI rich stream 166. The 2,2'-MDI rich stream 166 may be used in applications where trace amounts of aromatic amines are acceptable, such as non-food-grade applications. The 2,2'-MDI rich stream 166 may be used directly, or it may be blended with other process streams to create new products. In one embodiment, a new product is created by blending a portion of the 2,2'-MDI rich stream 166 with a portion of the purified 4,4'-MDI stream 155 at box 170. Prepolymers produced from this blend have low viscosity with extended curing time, which is beneficial in certain applications. In one embodiment, a new product is created in box 180 by blending a portion of the 2,2'-MDI rich stream 166 with the PMDI stream 144. The result is an isocyanate blend with extended curing time in flexible and rigid foam applications.

The bottom product of the separator 164 is removed in a purified 2,4'-MDI stream 168. As a result, the purified 2,4'-

MDI stream 168 includes a content of 2,4'-MDI of at least 52% by weight. In one example, the purified 2,4'-MDI stream 168 has a fraction containing at least 99% weight of MDI isomers with a content of 4,4'-MDI of from 5% to 48% weight, a content of 2,4'-MDI of from 52% to 95% weight, and a content of 2,2'-MDI of from 0.00% to 0.80% weight. A prepolymer produced from the purified 2,4'-MDI stream 168 has low viscosity and can be used in applications requiring low 2,2'-MDI content, such as polyurethane film composites and adhesives for product packaging in the food industry.

Figure 2:
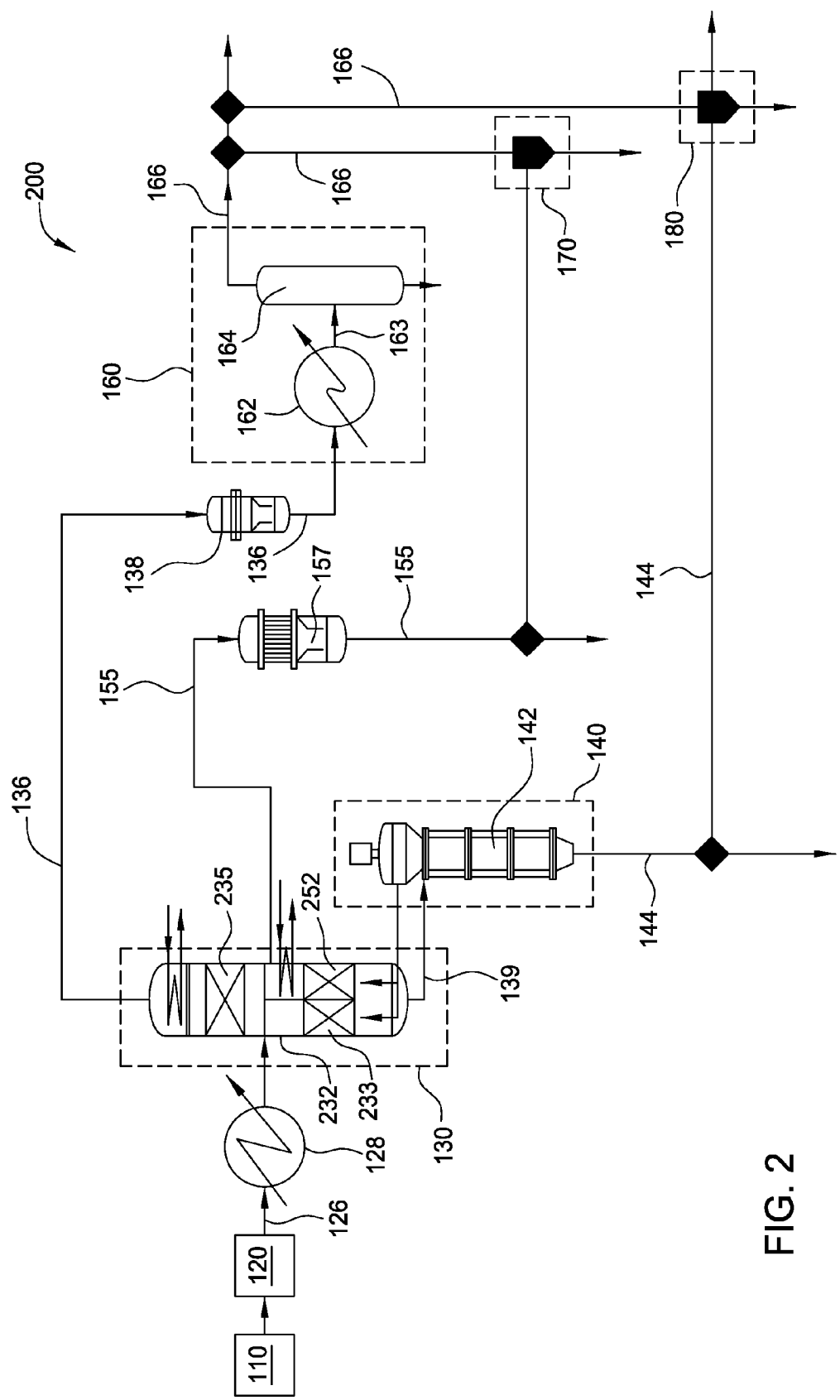
FIG. 2 is a partial schematic depiction of an apparatus and process 200 according to another embodiment.

FIG. 2 is a partial schematic depiction of an apparatus and process 200 according to another embodiment. Many of the steps of the process 200 are identical to those described above with respect to the process 100 depicted in FIG. 1. Thus, identical item numbers are used in FIG. 2 to represent the same processes and apparatus depicted and described with respect to FIG. 1. Referring to FIG. 2, the conventional operations and apparatus of boxes 110 and 120 are the same as those described with respect to FIG. 1.

The crude MDI feedstock 126, containing both MDI isomers and PMDI is heated to a temperature of between about 170° C. and about 260° C. in the heat exchanger 128. In box 230, the lower boiling point components are separated from the higher boiling point components as previously described with respect to FIG. 1. The preheated feedstock enters a distillation column 232. The distillation column 232 includes both a stripping section 233 and a rectification section 235, similar to the stripping section 133 and the rectification section 135 described with respect to FIG. 1.

Similar to that described with respect to FIG. 1, the 2,4'-MDI and 2,2'-MDI are recovered in the stripping section 233 and purified in the rectification section 235 of the distillation column 232. The result yields a 2,4'-MDI rich stream 136 having the same composition as that described with respect to FIG. 1.

The distillation column 232 further includes an integrated side rectification section 252, similar to side rectifier 152. A mixture of the 4,4'-MDI and the PMDI is removed from the distillation column 232 in bottoms 239 and sent to the evaporative reboiler 142 at box 140, similar to that described with respect to FIG. 1. In the evaporative reboiler 142, a portion of the mixture is evaporated and returned to the integrated side rectification section 252 of the distillation column 232. In the integrated side rectification section 252, 4,4'-MDI is separated from traces of PMDI remaining in the vapor. As a result, a purified 4,4'-MDI stream 155 exits the distillation column 232 and is passed through the quench condenser 157 as described with respect to FIG. 1. The operations and apparatus of boxes 160, 170, and 180, as well as the products produced therein are the same as those described with respect to FIG. 1.

In summary, embodiments of the present invention provide methods and apparatus for forming mixtures of MDI isomers with a low 2,2'-MDI isomer content and a high 2,4'-MDI isomer content. The resulting mixtures have an increased reactivity and are acceptable in food grade application due to the reduction in primary aromatic amines formed during the curing process. The process and apparatus also include controlling the amount of 4,4'-MDI, which is the most reactive isomer in the mixture allowing use in a wide variety of applications. In addition, the process and apparatus include forming mixtures of the MDI isomers with a high content of 2,2'-MDI, which can be mixed with PMDI or 4,4'-MDI for applications where lower viscosity and extended curing time are desired.

While the foregoing is directed to embodiments of the present invention, other and further embodiments of the invention may be devised without departing from the basic scope thereof, and the scope thereof is determined by the claims that follow.

The invention claimed is:

1. A process for the production of a mixture of methylene diphenyl diisocyanate (MDI) isomers, comprising:
    forming methylene diphenyl diamines and polyamines of the diphenylmethane series by reacting aniline and formaldehyde in the presence of an acid catalyst;
    phosgenating the methylene diphenyl diamines and polyamines of the diphenylmethane series to produce a mixture of the MDI isomers and polymeric MDI;
    heating the mixture of the MDI isomers and polymeric MDI to a temperature between about 170° C. to about 260° C.
    separating from the heated mixture of the MDI isomers and the polymeric MDI a first fraction containing at least 98% by weight of the MDI isomers comprising at least 52% by weight of 2,4'-MDI and 2,2'-MDI based on the total weight of the first fraction, of which a content of 4,4'-MDI in the first fraction is from 5% to 48% by weight, a content of 2,4'-MDI in the first fraction is from 52% to 95% by weight, and a content of 2,2'-MDI in the first fraction is from 0.01% to 20% by weight;
    heating the first fraction to a temperature between about 150° C. and about 190° C.;
    separating from the heated first fraction a second fraction containing at least 99% by weight of the MDI isomers comprising at least 52% by weight of 2,4'-MDI based on the total weight of the second fraction, of which a content of 4,4'-MDI in the second fraction is from 5% to 48% by weight, a content of 2,4'-MDI in the second fraction is from 52% to 95% by weight, and a content of 2,2'-MDI in the second fraction is from 0.00% to 0.80% by weight; and
    after removing the first fraction, a third fraction is separated from the heated mixture of MDI isomers and polymeric MDI using an evaporative reboiler and a side rectifier, the third fraction having a content of 4,4'-MDI in the third fraction of at least 98.5% by weight based on the total weight of the third fraction.

2. The process of claim 1, wherein after removing the first fraction, polymeric MDI is separated from the heated mixture of MDI isomers and polymeric MDI using the evaporative reboiler.

3. The process of claim 1, wherein the separating of the first fraction from the heated mixture of the MDI isomers and the polymeric MDI uses a distillation column.

4. The process of claim 1, wherein the side rectifier is an integrated side rectification section.

5. The process of claim 1, further comprising separating from the second fraction a fourth fraction comprising at least 52% of 2,2'-MDI.

6. The process of claim 5, further comprising blending a portion of the fourth fraction with a portion of the third fraction.

7. The process of claim 5, further comprising blending a portion of the fourth fraction with the polymeric MDI.

8. The process of claim 1, wherein an apparatus for separating from the mixture of MDI isomers and polymeric MDI the first fraction includes
    a distillation column having a stripping section and a rectification section; and
    a reboiler positioned to receive bottoms from the distillation column and send 4,4'-MDI to the side rectifier.

9. The process of claim 8, wherein a separator removes 2,2'-MDI from a condensate from the distillation column.

10. The process of claim 1, wherein the separating of the second fraction from the heated first fraction uses a distillation column.

11. The process of claim 1, wherein the evaporative reboiler is maintained at a temperature between about 100° C. and about 260° C. and a pressure between about 3 mmHg and about 30 mmHg.

12. The process of claim 1, wherein the side rectifier is maintained at a temperature between about 50° C. to about 250° C. and a pressure between about 1 mmHg and about 29 mm Hg.

* * * * *